(12) United States Patent
Kim et al.

(10) Patent No.: US 11,986,332 B2
(45) Date of Patent: May 21, 2024

(54) MULTI-PANEL DETECTOR AND IMAGING SYSTEM INCLUDING THE SAME

(71) Applicant: VIEWORKS CO., LTD., Anyang-si (KR)

(72) Inventors: In Dong Kim, Yongin-si (KR); Su Hyeon An, Gwangju (KR)

(73) Assignee: VIEWORKS CO., LTD., Anyang-si (KR)

( * ) Notice: Subject to any disclaimer, the term of this patent is extended or adjusted under 35 U.S.C. 154(b) by 71 days.

(21) Appl. No.: 17/864,917

(22) Filed: Jul. 14, 2022

(65) Prior Publication Data
US 2023/0016805 A1 Jan. 19, 2023

(30) Foreign Application Priority Data
Jul. 15, 2021 (KR) .......................... 10-2021-0093092

(51) Int. Cl.
*A61B 6/42* (2024.01)
*A61B 6/00* (2024.01)

(52) U.S. Cl.
CPC .......... *A61B 6/4266* (2013.01); *A61B 6/5241* (2013.01)

(58) Field of Classification Search
CPC ... A61B 6/4266; A61B 6/5241; A61B 6/4405; A61B 6/4411
See application file for complete search history.

(56) References Cited

U.S. PATENT DOCUMENTS

| 7,265,355 B2* | 9/2007 | Chang | A61B 6/5241 378/162 |
| 2006/0219926 A1* | 10/2006 | Shoji | H04N 25/41 250/370.09 |
| 2009/0238341 A1* | 9/2009 | Kawamura | A61B 6/04 378/162 |
| 2013/0114790 A1* | 5/2013 | Fabrizio | A61B 6/5241 378/189 |
| 2016/0135766 A1* | 5/2016 | Tateishi | A61B 6/4266 250/370.09 |

(Continued)

FOREIGN PATENT DOCUMENTS

| JP | 2006-141904 A | 6/2006 |
| JP | 4574202 B2 | 11/2010 |

(Continued)

OTHER PUBLICATIONS

Translated JP-2016202251 (Year: 2016).*
Korean Office Action dated May 16, 2023, in the counterpart Korean Patent Application No. 10-2021-0093092.

*Primary Examiner* — Dani Fox
*Assistant Examiner* — Soorena Kefayati
(74) *Attorney, Agent, or Firm* — Rabin & Berdo, P.C.

(57) ABSTRACT

Provided are a multi-panel detector including a marker to accurately match images photographed on a plurality of panels, and an imaging system including the same. A detector according to an exemplary embodiment of the present invention includes: a panel unit including a first panel and a second panel disposed while partially overlapping a rear portion of an end of the first panel; at least one marker disposed between a front portion of the first panel and a front portion of the second panel; and a radiation transmitting part formed at an end of the first panel and provided with the marker.

17 Claims, 6 Drawing Sheets

(56) References Cited

U.S. PATENT DOCUMENTS

| | | | | |
|---|---|---|---|---|
| 2016/0278722 A1* | 9/2016 | Tagawa | ................ | A61B 6/5241 |
| 2016/0287195 A1* | 10/2016 | Tagawa | ................ | A61B 6/4452 |
| 2019/0223818 A1* | 7/2019 | Suzuki | ................ | G06T 3/4007 |
| 2019/0320990 A1* | 10/2019 | Yamada | ................ | A61B 6/4266 |
| 2020/0121270 A1* | 4/2020 | Wojcik | ................ | A61B 6/0407 |

FOREIGN PATENT DOCUMENTS

| | | | | |
|---|---|---|---|---|
| JP | 4817067 | B2 | | 11/2011 |
| JP | 2011224337 | A | | 11/2011 |
| JP | 2016-104116 | A | | 6/2016 |
| JP | 2016202251 | A | * | 12/2016 |
| WO | 2019175865 | A1 | | 9/2019 |

\* cited by examiner

MULTI-PANEL DETECTOR AND IMAGING SYSTEM INCLUDING THE SAME

CROSS-REFERENCE TO RELATED APPLICATIONS

This application claims priority to and the benefit of Korean Patent Application No. 10-2021-0093092 filed in the Korean Intellectual Property Office on Jul. 15, 2021, the entire contents of which are incorporated herein by reference.

TECHNICAL FIELD

The present invention relates to a detector, and particularly, to a multi-panel detector including a marker, and an imaging system including the same.

BACKGROUND ART

In analog radiographic equipment using traditional film, images can be captured at once by using a large cassette and film for whole body capturing of a patient. In digital radiographic equipment, a system capable of acquiring a radiographic image of a patient's whole body with one shot by connecting a plurality of detectors is being commercialized and sold.

In acquiring a radiographic image by using the digital radiographic equipment, a technique for synthesizing a plurality of radiographic images captured by overlapping some regions into one image by using a stitching technique is mainly used.

The digital radiographic equipment using the stitching technique in the related art uses a method of moving a single detector panel up and down or left and right to enable photographing of the patient's whole body or upper/lower body through imaging two times or more.

However, according to the digital radiographic equipment in the related art, for stitching photography, the single detector panel has to move up and down or left and right from the bottom or rear of the patient, so there is a problem that the photographing time is long, and in addition, there is a disadvantage that an additional driving unit for moving the detector panel is required.

In some of the digital radiation equipment in the related art, a ruler is installed between a patient and the detector panel to increase the stitching precision. In the case of installing the ruler, not only the ruler must be installed in the entire stitching area, but when the ruler is attached to the front surface of the detector, there is a problem in that the ruler that is not related to the object to be actually photographed appears in the image.

PRIOR ART LITERATURE

Patent Document

Japanese Patent No. 4817067

SUMMARY OF THE INVENTION

The present invention has been made in an effort to provide a multi-panel detector which includes a marker to accurately match images photographed on a plurality of panels, and an imaging system including the same.

The present invention has been made in an effort to provide a multi-panel detector which is capable of excluding a marker from a finally matched image, and an imaging system including the same.

An exemplary embodiment of the present invention provides a detector including: a panel unit including a first panel and a second panel disposed while partially overlapping a rear portion of an end of the first panel; at least one marker disposed between a front portion of the first panel and a front portion of the second panel; and a radiation transmitting part formed at an end of the first panel and provided with the marker.

The front portion of the second panel may be disposed while partially overlapping a rear portion of the radiation transmitting part.

The radiation transmitting part may have higher radiation transmittance than radiation transmittance of a frame portion of the first panel.

The first panel may include: a first detection unit disposed in the first panel; and a second detection unit disposed within the first panel and disposed while partially overlapping a rear portion of an end of the first detection unit.

The marker may be located between the second detection unit and the front portion of the second panel.

The marker may be formed of a material with low radiation transmittance.

The markers may be formed in plurality and have different shapes from each other.

The second panel may include a third detection unit disposed within the second panel.

The panel unit may include three or more panels.

Each of the first panel and the second panel may include one detection unit or a plurality of detection units inside thereof.

Another exemplary embodiment of the present invention provides an imaging system, including: a detector including a first panel and a second panel; a radiation generating unit for emitting radiation to the detector; an image processing unit for matching an image acquired by the first panel with an image acquired by the second panel based on a marker formed on the first panel; and an image display unit for displaying the matched image to a user.

The image processing unit may include: a marker position recognizing unit for recognizing and storing a position of the marker disposed between the front portion of the first panel and the front portion of the second panel when the radiation is emitted from the radiation generating unit; and an image matching unit for matching an image acquired by the first panel and an image acquired by the second panel based on the position of the marker recognized by the marker position recognition unit and a position of the marker in the image acquired by the second panel.

The image matching unit may be configured to match the image acquired by the first panel with the image acquired by the second panel except for an area in which the marker appears from the image acquired by the second panel.

According to the present invention, there is the advantage in that it is possible to easily align and combine an image acquired by the front panel and an image acquired by the rear panel based on the position of the marker disposed between the front portion of the front panel and the front portion of the rear panel and the position of the marker in the image acquired by the rear panel.

Since the image matching unit of the present invention is capable of matching the image acquired by the front panel with the image acquired by the rear panel except for the area where the marker appears in the image acquired by the rear panel, the marker is not displayed in the image finally matched by the image matching unit, thereby acquiring an accurate image without artifacts.

When a plurality of markers is configured, the shapes of the markers are different from each other, so that it is possible to easily distinguish the left and the right of the finally matched stitching image.

Since the present invention may include a plurality of panels, and each panel may include one or more detection units, it is possible to implement a system capable of imaging even a long to-be-examined subject.

The foregoing summary is illustrative only and is not intended to be in any way limiting. In addition to the illustrative aspects, embodiments, and features described above, further aspects, embodiments, and features will become apparent by reference to the drawings and the following detailed description.

Figure 1:
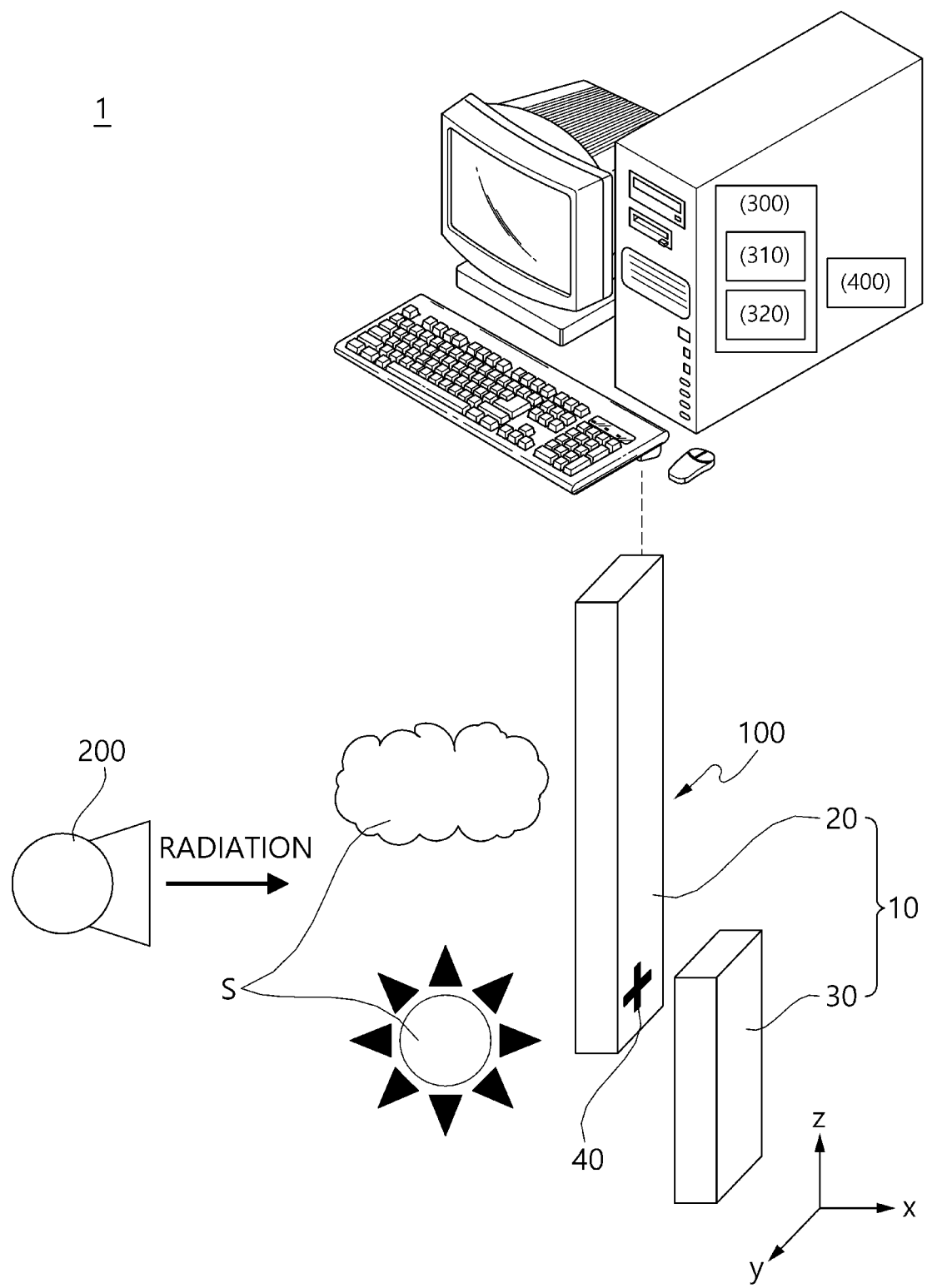
FIG. 1 is a diagram illustrating a detector and an imaging system including the detector according to an exemplary embodiment of the present invention.

It should be understood that the appended drawings are not necessarily to scale, presenting a somewhat simplified representation of various features illustrative of the basic principles of the invention. The specific design features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DETAILED DESCRIPTION

Hereinafter, exemplary embodiments of the present invention will be described in detail with reference to the accompanying drawings. First of all, it should be noted that in giving reference numerals to elements of each drawing, like reference numerals refer to like elements even though like elements are illustrated in different drawings. Further, in the following description of the present invention, a detailed description of known configurations or functions incorporated herein will be omitted when it is judged that the detailed description may make the subject matter of the present disclosure unclear. It should be understood that although the exemplary embodiment of the present invention is described hereafter, the spirit of the present invention is not limited thereto and the present invention may be changed and modified in various ways by those skilled in the art.

Figure 2:
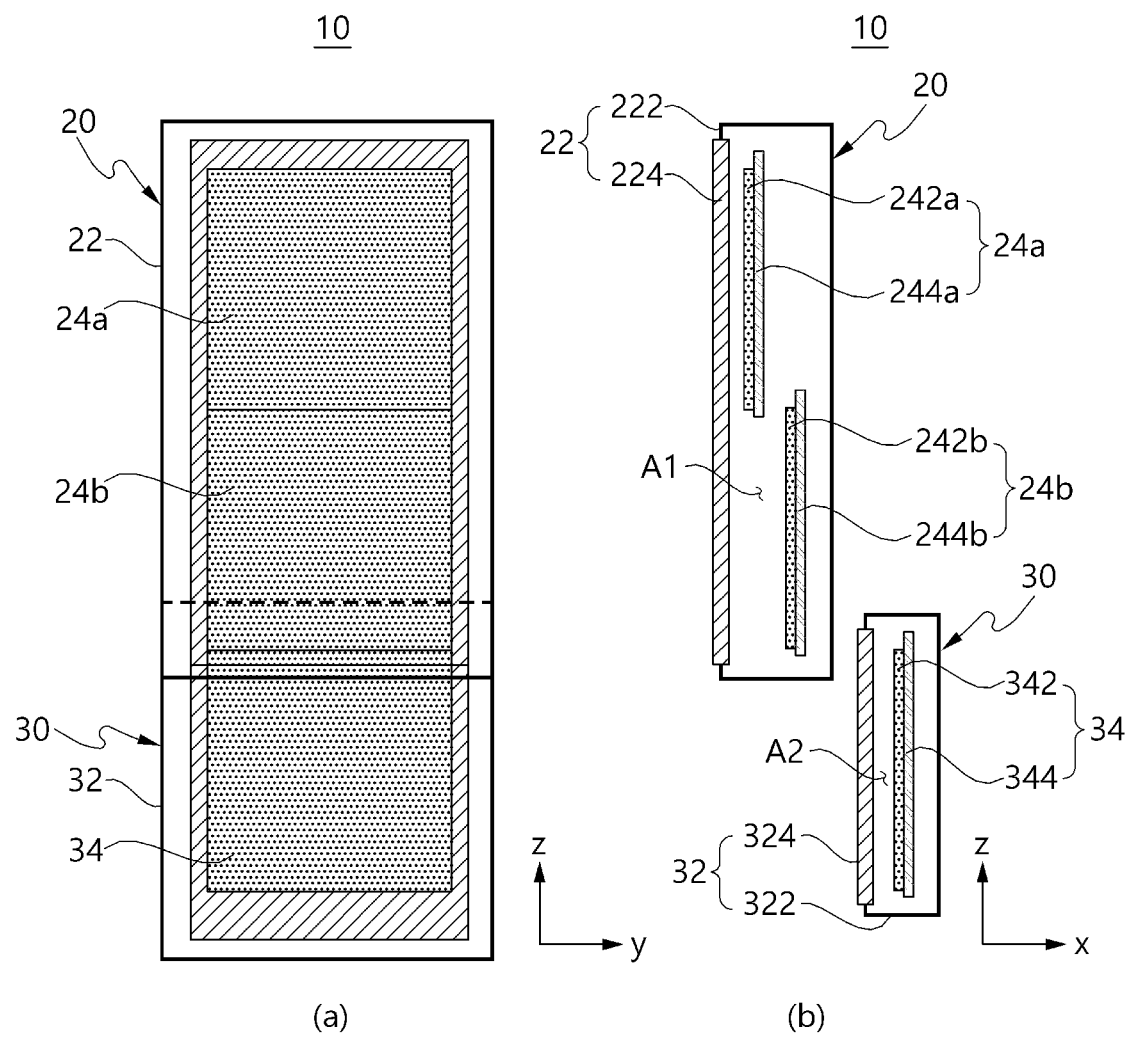
FIG. 2 is a diagram illustrating a schematic shape of the detector according to the exemplary embodiment of the present invention.

FIG. 1 is a diagram illustrating a detector 100 and an imaging system 1 including the detector according to an exemplary embodiment of the present invention, and FIG. 2 is a diagram illustrating a schematic shape of the detector 100 according to the exemplary embodiment of the present invention. In detail, (a) of FIG. 2 is a diagram schematically illustrating the inside of the detector 100 viewed from the front, and (b) of FIG. 2 is a diagram schematically illustrating the inside of the detector 100 viewed from the side.

In FIGS. 1 and 2, the X-axis direction indicates the thickness direction, the Z-axis direction indicates the vertical direction, and the direction perpendicular to both the X-axis and the Z-axis indicates the Y-axis direction (horizontal direction).

Referring to FIG. 1, an imaging system 1 according to the exemplary embodiment of the present invention includes a detector 100, a radiation generating unit 200, an image processing unit 300, and an image display unit 400.

The detector 100 may be a device for converting the energy transported by the radiation (X-rays, gamma rays, and the like) into an electric signal (charge signal) to obtain image information. For example, the detector 100 converts light (visible light) emitted by a fluorescent material in response to radiation that has passed through a to-be-examined subject S into an electric signal (charge signal) to obtain image information.

As illustrated in FIG. 1, the detector 100 includes a panel unit 10 including a first panel 20 (front panel) and a second panel 30 (rear panel) and at least one marker 40. As an example, the panel unit 10 may be supported in vertical and horizontal directions through a separate support frame (not illustrated).

The radiation generating unit 200 emits radiation which passes through the to-be-examined subject S and irradiates the detector 100.

The image processing unit 300 may match an image acquired by the first panel 20 with an image acquired by the second panel 30. The image processing unit 300 may synthesize the image acquired by the first panel 20 and the image acquired by the second panel 30 by matching the images.

The image display unit 400 may display the matched or synthesized image to a user.

As an example, the image processing unit 300 and the image display unit 400 may be provided in a Personal Computer (PC) that is provided separately from the detector 100, but the present invention is not limited thereto. In this case, the manipulation of the image processing unit 300 and the image display unit 400 may be performed by a user or may be performed automatically by an automated system.

On the other hand, the second panel 30 of the detector 100 may be disposed to partially overlap a rear portion of an end of the first panel 20 (the lower end of the first panel 20).

However, the exemplary embodiment of the present invention is not limited thereto, and the marker 40 may be located not only at the lower end of the first panel 20, but also at the side end or upper end of the first panel 20, and thus the second panel 30 may also be disposed while a portion of the second panel 30 overlaps the side end or upper end of the first panel 20.

Preferably, the marker 40 may be made of a material having low radiation transmittance.

Referring to FIG. 2, the first panel 20 and the second panel 30 include panel cases 22 and 32 including frame portions 222 and 322 and front cover portions 224 and 324 coupled to openings of the frame portions 222 and 322, respectively.

Preferably, the front cover portions 224 and 324 may be formed of a lightweight material that allows X-rays to transmit, and may be made of, for example, carbon fiber reinforced plastics (CFRP), and may be stably fixed to the frame portion 222 by means of a fixing means, such as a screw. In addition, the front cover portions 224 and 324 may have a rectangular flat plate shape, but are not limited thereto.

Referring to FIG. 2, the end of the front cover portion 324 of the second panel 30 (the upper end of the front cover portion 324 of the second panel 30) may be disposed while partially overlapping the rear portion of the end of the panel case 22 of the first panel 20 (the lower end of the panel case 22 of the first panel 20).

However, the exemplary embodiment of the present invention is not limited thereto, and the marker 40 may be located at the side end or the upper end of the panel case 22 of the first panel 20, and accordingly, the second panel 30 may also be disposed to partially overlap the side end or the upper end of the panel case 22 of the first panel 20.

Figure 3:
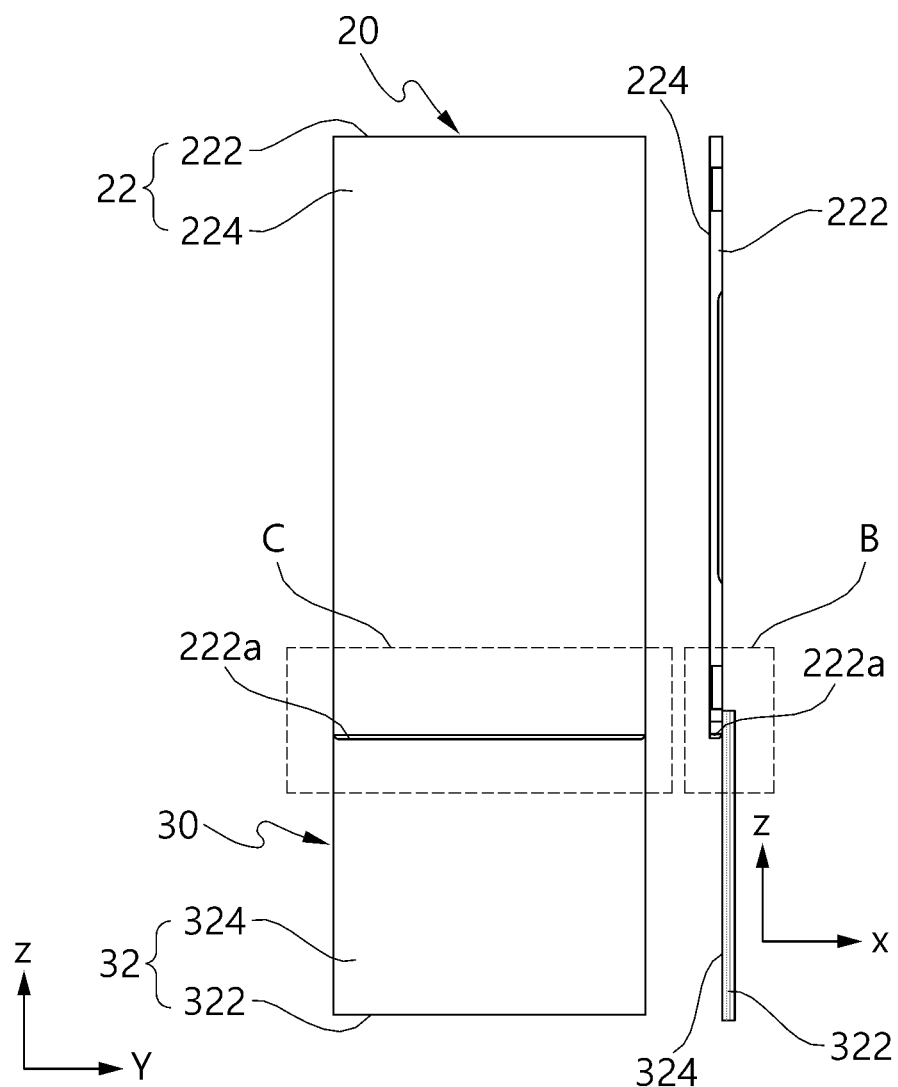
FIGS. 3 to 5 are diagrams illustrating the detailed shape of the detector according to the exemplary embodiment of the present invention.
Figure 4:
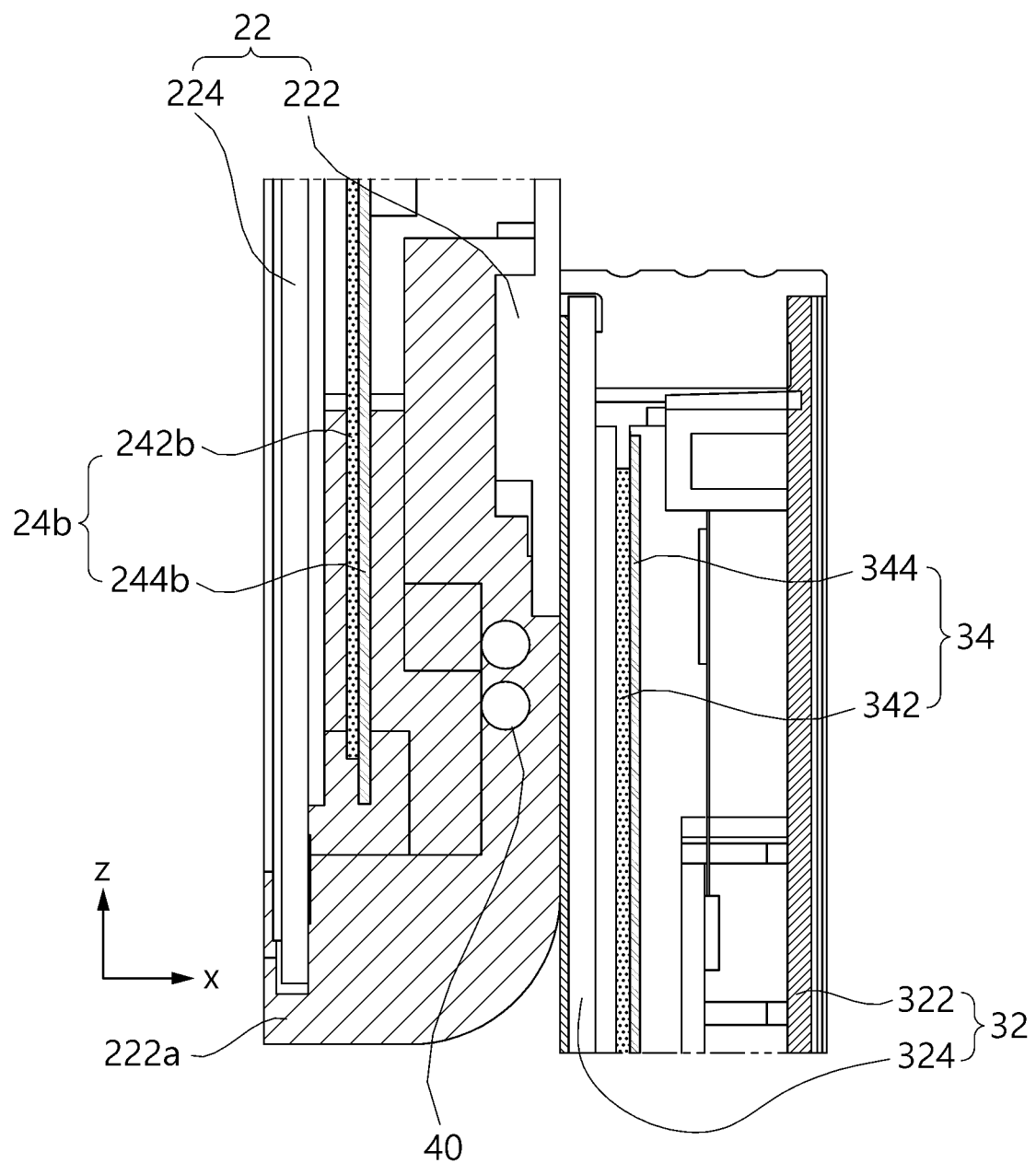
Figure 5:
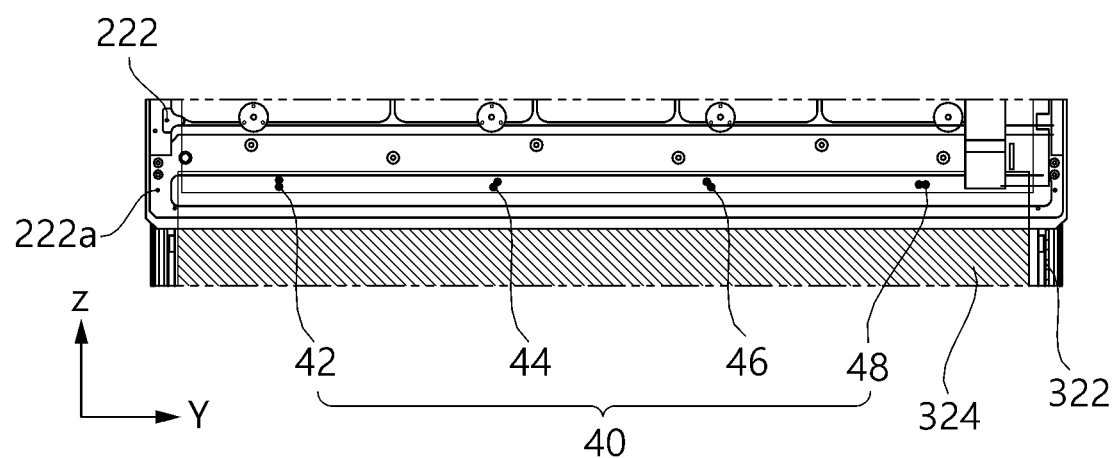

FIGS. 3 to 5 are diagrams illustrating the detailed shape of the detector 100 according to the exemplary embodiment of the present invention. In detail, FIG. 3 is a diagram illustrating the detector 100 viewed from the front and the side, and FIG. 4 is an enlarged diagram of part B of FIG. 3 (a perspective view illustrating the inside of a part of the side of the detector 100), and FIG. 5 is an enlarged diagram of part C of FIG. 3 (a perspective view illustrating the inside of a part of the front of the detector 100).

Referring to FIGS. 3 to 5, a radiation transmitting part 222a may be formed at the end of the first panel 20 (a lower end of the first panel 20).

More specifically, at the end of the frame portion 222 of the first panel 20 (the lower end of the frame portion 222 of the first panel 20), the radiation transmitting part 222a having higher radiation transmittance than that of the frame portion 222 of the first panel 20 may be coupled in the vertical direction (Z-axis direction) perpendicular to the thickness direction (X-axis direction).

However, the formation position of the radiation transmitting part 222a is not limited to the lower end of the first panel 20, and may also be located at the side end or the upper end of the first panel 20.

As an example, the radiation transmitting part 222a may be coupled to the end of the frame portion 222 of the first panel 20 by a method, such as screwing, but the present invention is not limited thereto, and the radiation transmitting part 222a may be integrally formed with the frame portion 222 of the first panel 20.

The above-described marker 40 may be formed in the radiation transmitting part 222a. As an example, at least one groove is formed in the radiation transmitting part 222a, and the ball-shaped marker 40 may be inserted into the groove formed in the radiation transmitting part 222a, but the present invention is not limited thereto.

The front portion of the second panel 30 may be disposed such that a portion (the upper end of the front portion of the second panel 30) overlaps the rear portion of the radiation transmitting part 222a.

In detail, the end of the front cover portion 324 of the second panel 30 (the upper end of the front cover portion 324 of the second panel 30) may be disposed while partially overlapping the rear portion of the radiation transmitting part 222a.

Referring to FIGS. 2 to 5, the first panel 20 further includes a first detection unit 24a which is disposed in an accommodation space A1 formed by the frame portion 222, the front cover portion 224, and the radiation transmitting part 222a of the first panel 20, and a second detection unit 24b disposed in the accommodation space A1 and disposed so as to partially overlap a rear portion of the end of the first detection unit 24a (the lower end of the first detection unit 24a).

However, the disposed position of the second detection unit 24b is not limited thereto, and the second detection unit 24b may also be disposed while partially overlapping the side end or the upper end of the first detection unit 24a.

In an exemplary embodiment, the first detection unit 24a and the second detection unit 24b include scintillators 242a and 242b and photoelectric conversion panels 244a and 244b disposed below the scintillators 242a and 242b, respectively.

The scintillators 242a and 242b are made of a fluorescent material that emits light (visible light) in response to the radiation passing through the to-be-examined subject S, and the photoelectric conversion panels 244a and 244b may convert light (visible light) generated by the scintillators 242a and 242b into an electric (charge) signal and output the electric (charge) signal.

The photoelectric conversion panels 244a and 244b include photoelectric conversion elements (not illustrated) in a photodiode-based matrix array and a switch element (not illustrated) for controlling conduction between the photoelectric conversion elements. As an example, the switch element includes a Thin Film Transistor (TFT).

Although not illustrated, the first detection unit 24a and the second detection unit 24b may further include a substrate unit which receives an electric signal transmitted from the outside and generates a control signal to enable the first detection unit 24a and the second detection unit 24b to operate.

On the other hand, it is disclosed that the detector 100 according to the exemplary embodiment of the present invention uses an indirect conversion method of emitting light in response to radiation by using the scintillator, and then converting the light generated by the scintillator into an electric signal through the photoelectric conversion panel and outputting the converted electric signal, but the detector 100 is not limited thereto, and may also be a detector using a direct conversion method of directly converting incident radiation into an electric signal without a separate scintillator.

Although it has been illustrated and described that two detection units (the first detection unit 24a and the second detection unit 24b) are provided inside the first panel 20, the present invention is not limited thereto, and one detection unit or three or more detection units may be provided inside the first panel 20.

The second panel 30 further includes a third detection unit 34 disposed in an accommodation space A2 formed by the frame portion 322 and the front cover portion 324 of the second panel 30.

In an exemplary embodiment, the third detection unit 34 includes a scintillator 342 and a photoelectric conversion panel 344 similar to the first detection unit 24a or the second detection unit 24b described above.

In this case, the configurations of the scintillator 342 and the photoelectric conversion panel 344 provided in the third detection unit 34 are the same as those of the scintillators 242a and 242b and the photoelectric conversion panels 244a and 244b of the first detection unit 24a and the second detection unit 24b described above, so that a detailed description thereof will be omitted.

Meanwhile, although it has been illustrated and described that one detection unit (the third detection unit 34) is provided inside the second panel 30, the present invention is not limited thereto, and two or more detection units may also be provided.

Referring to FIG. 4, the marker 40 may be positioned between the second detection unit 24*b* and the front surface of the second panel 30.

In detail, the marker 40 may be positioned between the second detection unit 24*b* and an end of the front cover portion 324 of the second panel 30.

For example, in case that the marker 40 is disposed between the detection unit (for example, the second detection unit 24*b*) disposed the lowermost side among the detection units disposed in the first panel 20 and the front portion of the second panel 30, the marker 40 may be formed at any position (the lower end, the side end, or the upper end of the first panel 20) of the first panel 20.

In addition, the marker 40 may be provided as a single marker, but may be formed in plurality as illustrated in FIG. 5 and may have different shapes from each other.

For example, as illustrated in FIG. 5, the marker 40 may include at least one of a first marker 42 in which two balls are arranged side by side in a vertical direction, a second marker 44 in which two balls are arranged to be inclined at a predetermined angle in one direction, a third marker 46 in which two balls are arranged to be inclined at a predetermined angle in a direction opposite to one direction, and a fourth marker 48 in which two balls are arranged side by side in a horizontal direction. However, the shape and the number of markers are not limited thereto.

As illustrated in FIG. 5, when the shapes of the plurality of markers 40 are formed differently, the left and right sides of the stitched image to be matched later by the image processing unit 300 may be easily distinguished.

Since the marker 40 is located at the end (the lower end of the first panel 20) of the front panel (the first panel 20), and is located to be adjacent to the detection unit (the second detection unit 24*b*) located at the lowermost side between the two detection units located inside the front panel, when the detection unit of the same structure is additionally applied, three or more detection units are provided inside the front panel, two or more detection units are also provided inside the rear panel (the second panel 30), and the marker 40 is disposed to be adjacent to the lowermost detection unit among the plurality of detection units of the front panel, so that it is possible to implement the system capable of imaging even a long to-be-examined subject S.

In the panel unit 10 of the detector 100 according to the exemplary embodiment of the present invention described above, the first panel 20 and the second panel 30 are illustratively described, but the present invention is not limited thereto, and three or more panels may be provided.

For example, the panel unit 10 has the configuration in which at least one marker 40 is formed between the front portion of the first panel 20 and the front portion of the second panel 30, and at least one marker is formed between the front portion of the second panel 30 and the front portion of the third panel (not illustrated), and three or more panels may be provided. In this case, it is possible to implement a system capable of imaging even the to-be-examined subject S having a longer length.

Figure 6:
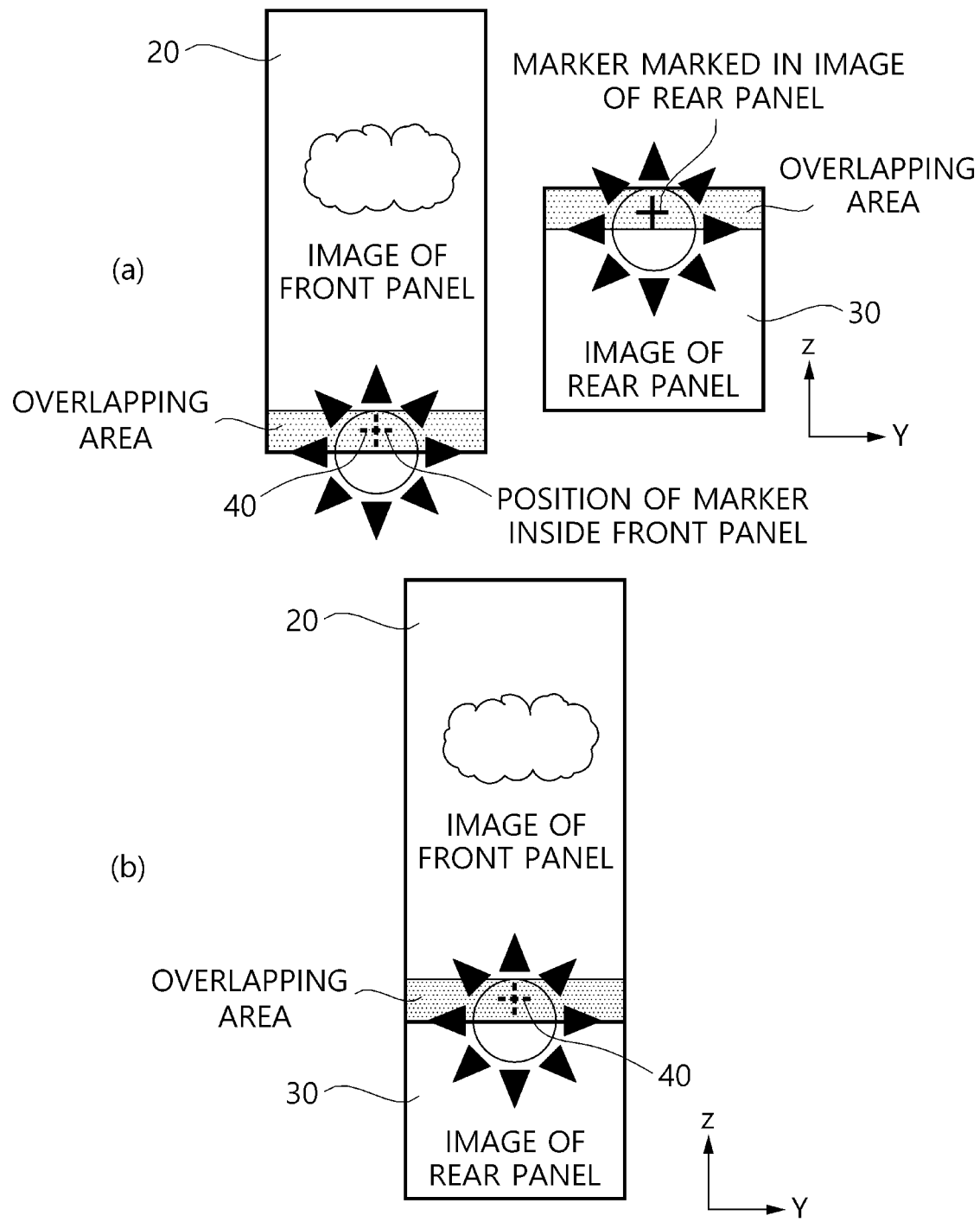
FIG. 6 is a diagram illustrating a process of aligning and combining an image acquired by a first panel and an image acquired by a second panel by using a marker.

FIG. 6 is a diagram illustrating a process of aligning and combining an image acquired by the first panel 20 and an image acquired by the second panel 30 by using the marker 40.

In detail, in FIG. 6, (a) of FIG. 6 shows a state before the images acquired by the first panel 20 (the front panel) and the second panel 30 (the rear panel) are aligned, and (b) of FIG. 6 illustrates a state in which the images acquired by the first panel 20 and the second panel 30 are aligned and combined.

Referring to FIGS. 1 and 6, the image processing unit 300 may match the image acquired by the first panel 20 and the image acquired by the second panel 30 based on the marker formed on the first panel 20.

The image processing unit 300 includes a marker position recognition unit 310 for recognizing and storing the position of the marker 40 disposed between the front portion of the first panel 20 and the front portion of the second panel 30 when the radiation is emitted from the radiation generating unit 200, and an image matching unit 320 for matching the image acquired by the first panel 20 and the image acquired by the second panel 30 based on the position of the marker 40 recognized by the marker position recognition unit 310 and the position of the marker 40 in the image obtained by the second panel 30.

In detail, the marker position recognition unit 310 may recognize and store the position of the marker 40 disposed between the second detection unit 24*b* of the first panel 20 and the front portion of the second panel 30.

The position of the marker 40 recognized by the marker position recognition unit 310 may be indicated as illustrated in (a) of FIG. 6 (refer to the cross-shaped dotted line).

The marker 40 is positioned between the front portion of the first panel 20 and the front portion of the second panel 30 as illustrated in FIGS. 3 to 5, and in particularly, the marker 40 is located between the second detection unit 24*b* and the front portion of the second panel 30, so that the marker 40 does not appear in the image acquired by the first panel 20.

On the other hand, the marker 40 may appear in the image acquired by the second panel 30 as illustrated in (a) of FIG. 6 (in detail, the marker 40 appears in the upper end of the image acquired by the second panel 30) (see the cross-shaped solid line).

The image matching unit 320 may match the image acquired by the first panel 20 with the image acquired by the second panel 30 based on the marker 40 formed on the first panel 20.

Thereafter, the image display unit 400 may display the image matched by the image matching unit 320 of the image processing unit 300 to the user as illustrated in (b) of FIG. 6.

In this case, since the area in which the marker 40 appears in the image acquired by the second panel 30 (the upper end of the image acquired by the second panel 30) is an "overlapping area" with the area (the end of the first panel 20 (the lower end of the first panel 20)) in which the marker 40 formed in the first panel 20 is located, as illustrated in (b) of FIG. 6, in the final image in which the image acquired by the first panel 20 and the image acquired by the second panel 30 are matched by the image matching unit 320, the marker 40 is not displayed (see the cross-shaped dotted line).

In detail, the image matching unit 320 may match the image acquired by the first panel 20 and the image acquired by the second panel 30 based on the position of the marker 40 recognized by the marker position recognition unit 310 and the position of the marker 40 in the image acquired by the second panel 30. The image matching unit 320 may match the image acquired by the first panel 20 and the image acquired by the second panel 30, except for the area in which the marker 40 appears in the image acquired by the second panel 30, so that the marker 40 is not displayed in the finally synthesized image.

Accordingly, in the present invention, there is an advantage in that it is possible to acquire an image without artifacts by the above-described configuration.

The image acquired by the first panel 20 and the image acquired by the second panel 30 are matched based on the position of the marker 40 disposed between the front portion of the first panel 20 and the front portion of the second panel 30 and the position of the marker 40 in the image acquired by the second panel 30, so that it is possible to correct left and right deviations of the image acquired by the first panel 20 and the image acquired by the second panel 30 during image matching by the image matching unit 320.

Although the exemplary embodiment of the present invention has been described for illustrative purposes, those skilled in the art will appreciate that various modifications, additions and substitutions are possible, without departing from the essential characteristic of the invention. Therefore, the exemplary embodiments disclosed in the present invention and the accompanying drawings are not intended to limit the technical spirit of the present invention, but are intended to illustrate the scope of the technical idea of the present invention, and the scope of the present invention is not limited by the exemplary embodiment and the accompanying drawings. The scope of the present invention shall be construed on the basis of the accompanying claims in such a manner that all of the technical ideas included within the scope equivalent to the claims belong to the scope of the present invention.

As described above, the exemplary embodiments have been described and illustrated in the drawings and the specification. The exemplary embodiments were chosen and described in order to explain certain principles of the invention and their practical application, to thereby enable others skilled in the art to make and utilize various exemplary embodiments of the present invention, as well as various alternatives and modifications thereof. As is evident from the foregoing description, certain aspects of the present invention are not limited by the particular details of the examples illustrated herein, and it is therefore contemplated that other modifications and applications, or equivalents thereof, will occur to those skilled in the art. Many changes, modifications, variations and other uses and applications of the present construction will, however, become apparent to those skilled in the art after considering the specification and the accompanying drawings. All such changes, modifications, variations and other uses and applications which do not depart from the spirit and scope of the invention are deemed to be covered by the invention which is limited only by the claims which follow.

What is claimed is:

1. A detector, comprising:
    a panel unit including a first panel and a second panel partially overlapping a rear portion of an end of the first panel;
    at least one marker disposed between a front portion of the first panel and a front portion of the second panel; and
    a radiation transmitting part formed at the end of the first panel and provided with the at least one marker;
    wherein the first panel includes:
        a first detection unit disposed in the first panel; and
        a second detection unit disposed within the first panel and partially overlapping a rear portion of an end of the first detection unit.

2. The detector of claim 1, wherein the front portion of the second panel partially overlaps a rear portion of the radiation transmitting part.

3. The detector of claim 1, wherein the at least one marker is located between the second detection unit and the front portion of the second panel.

4. The detector of claim 1, wherein the at least one marker is formed of a material with low radiation transmittance.

5. The detector of claim 1, wherein the at least one markers is formed as a plurality of markers and the plurality of markers have different shapes from each other.

6. The detector of claim 1, wherein the second panel includes a third detection unit disposed within the second panel.

7. The detector of claim 1, wherein the panel unit includes three or more panels.

8. The detector of claim 1, wherein each of the first panel and the second panel includes one detection unit or a plurality of detection units inside thereof.

9. The detector of claim 2, wherein the radiation transmitting part has a higher radiation transmittance than a radiation transmittance of a frame portion of the first panel.

10. An imaging system, comprising:
    a detector including a first panel and a second panel;
    a radiation generating unit for emitting radiation to the detector;
    an image processing unit for matching an image acquired by the first panel with an image acquired by the second panel based on a marker formed on the first panel; and
    an image display unit for displaying the matched image to a user,
    wherein the second panel partially overlaps a rear portion of the first panel,
    wherein the marker is disposed between a front portion of the first panel and a front portion of the second panel,
    wherein the detector further includes a radiation transmitting part formed at an end of the first panel and provided with the marker,
    wherein the image processing unit includes:
        a marker position recognizing unit for recognizing and storing a position of the marker disposed between the front portion of the first panel and the front portion of the second panel when the radiation is emitted from the radiation generating unit; and
        an image matching unit for matching the image acquired by the first panel and the image acquired by the second panel based on the position of the marker recognized by the marker position recognition unit and a position of the marker in the image acquired by the second panel, and
    wherein the image matching unit is configured to match the image acquired by the first panel with the image acquired by the second panel except for an area in which the marker appears from the image acquired by the second panel.

11. The imaging system of claim 10, wherein the front portion of the second panel partially overlaps a rear portion of the radiation transmitting part.

12. The imaging system of claim 10, wherein the first panel includes:
    a first detection unit disposed in the first panel; and
    a second detection unit disposed within the first panel and partially overlapping a rear portion of the first detection unit.

13. The imaging system of claim 10, wherein the marker is formed of a material with low radiation transmittance.

14. The imaging system of claim 10, wherein the marker is formed as a plurality of markers and the plurality of markers have different shapes from each other.

15. The imaging system of claim 10, wherein the second panel includes a third detection unit disposed within the second panel.

16. The imaging system of claim 11, wherein the radiation transmitting part has a higher radiation transmittance than a radiation transmittance of a frame portion of the first panel.

17. The imaging system of claim 12, wherein the marker is located between the second detection unit and the front portion of the second panel.

* * * * *